United States Patent [19]

Stein et al.

[11] 4,195,984

[45] Apr. 1, 1980

[54] HERBICIDES DERIVED FROM DIHALO ISONICOTINOYL DERIVATIVES OF AMINO ACIDS

[75] Inventors: Robert G. Stein, Kenosha, Wis.; Donald S. Kenney, Northbrook, Ill.

[73] Assignee: Abbott Laboratories, North Chicago, Ill.

[21] Appl. No.: 19,995

[22] Filed: Mar. 12, 1979

[51] Int. Cl.2 ........................ A01N 9/22; C07D 213/40

[52] U.S. Cl. .......................................... 71/94; 546/323

[58] Field of Search ............................. 546/323; 71/94

[56] References Cited

U.S. PATENT DOCUMENTS

| | | | |
|---|---|---|---|
| 3,755,339 | 8/1973 | McKendry | 71/94 X |
| 4,108,629 | 8/1978 | McKendry | 71/94 OR |

FOREIGN PATENT DOCUMENTS

| | | | |
|---|---|---|---|
| 2457971 | 6/1976 | Fed. Rep. of Germany | 546/323 |

OTHER PUBLICATIONS

Klingsberg, Pyridine and Its Derivatives, Part Three, pp. 250-251, 258-259, and 263-264, Interscience Publishers, NY (1962).

Gardner et al., J. Org. Chem., vol. 19, pp. 753 to 757 (1954).

Meyer et al., Chem. Abstracts, vol. 25, pp. 2999 to 3000 (1931).

Rapp et al., Biochemistry, vol. 5, pp. 4100 to 4105 (1966).

Uno et al., Chem. Abstracts, vol. 68, abst. 69294v (1968).

Swain et al., J. Am. Chem. Soc., vol. 79, pp. 5220 to 5253 (1957).

Vorontsov et al., Chem. Abstracts, vol. 81, abst. 147,614j (1974).

Yoshimoto et al., J. Org. Chem., vol. 41, pp. 2269-2273 (1976).

Koul et al., Chem. Abstracts, vol. 78, abst. 72,562t (1973).

*Primary Examiner*—John D. Randolph

*Attorney, Agent, or Firm*—Paul D. Burgauer; Robert L. Niblack

[57] ABSTRACT

New agriculturally useful compounds are described which are the 2,6-dibromo- or -dichloro- iso- nicotinoyl derivatives of aminoacids.

18 Claims, No Drawings

HERBICIDES DERIVED FROM DIHALO ISONICOTINOYL DERIVATIVES OF AMINO ACIDS

DETAILED DESCRIPTION OF THE INVENTION

The compounds of the present invention are represented by the formula

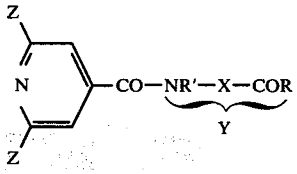

wherein Z is Br or Cl, R is OH, $NH_2$, NH-loweralkyl, NH-phenyl or N-diloweralkyl, R' is H or $CH_3$, X is phenylene, $>C(CH_3)_2$, $>CHCH_2CONH_2$, $-(CH_2)_n$,

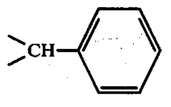 or 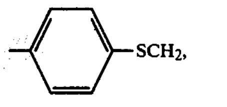

with n being an integer from 2–5, or wherein the moiety embraced as Y represents the acyl portion of a naturally occuring amino acid, and agriculturally acceptable acid addition salts thereof.

These compounds are useful as pre-emergence and post-emergence herbicides, plant growth regulators, herbicides and abscission agents, and many of them also increase the production of extractable sugar in sugar cane.

In a general embodiment, the compounds of Formula I are made by combining the chosen 2,6-disubstituted isonicotinoyl halide with an aqueous solution of the aminoacid R'NH-X-COOH or YOH in the presence of an acid acceptor and stirring the mixture until homogenecity is attained. The aminoacid and the isonicotinoyl halide are best used in an equimolar ratio or a 10% excess of either component; the acid acceptor should be present in a molar ratio of at least 2:1 over the isonicotinoyl component. The reaction proceeds satisfactorily at room temperature, although good results are obtained at temperatures of 0°–50° C. or higher, where the stability of the reactants allows temperatures above 50° C. When a clear solution is obtained, mineral acid is added to the reaction mixture, precipitating the desired compound (I). Where the above aminoacid component is R'NH-X-CONR''R''' and R'' is alkyl or phenyl and R''' is H or alkyl, only one molar equivalent of an acid acceptor is needed and (I) precipitates from the reaction mixture without the addition of a mineral acid.

Specific embodiments of the above process are shown in the following examples which, however, are illustrations only and are not intended to limit the invention in any respect.

EXAMPLE 1

(a) To an ice bath cooled solution of 11.2 g. of potassium hydroxide and 7.5 g. of glycine in 200 ml. of water is added, under stirring, 21 g. of 2,6-dichloroisonicotinoyl chloride. Stirring is continued until the solution is homogeneous and under continued cooling. Sufficient 6N-hydrochloric acid is added to reach a pH of 4. The precipitate is filtered, washed with cold water and recrystallized from ethanol/water to give 20 g. of solid, white N-(2,6-dichloroisonicotinoyl)glycine; m.p. 157°–8° C.

(b) When 2,6-dibromoisonicotinoyl chloride is used in an equimolar amount to the above dichloro- derivative, N-(2,6-dibromoisonicotinoyl)glycine is obtained; m.p. 151°–2° C.

EXAMPLE 2

A mixture of 14.05 g. of 2,6-dibromoisonicotinic acid and 11.9 g. of thionyl chloride is refluxed in 200 ml. of benzene for 4 hours. The clear solution is then concentrated in vacuo to give a brown oil. This crude acid chloride is dissolved in 50 ml. of benzene and added to a stirring mixture of 5.5 g. of glycinamide hydrochloride and 10.1 g. of triethylamine in 300 ml. of benzene. The mixture is refluxed 2 hours and then cooled. After successive washings with 5% aqueous HCl, water, 10% aqueous $NaHCO_3$, water, the solution is concentrated in vacuo to produce a tan solid. One recrystallization from ethanol gives 4.8 g. of colorless needles of N-(2,6-dibromoisonicotinoyl)glycinamide; m.p. 236°–7° C.

EXAMPLE 3

(a) To 200 ml. of water containing 15 g. of l-aspargine hydrate and 11.2 g. of KOH is added 21 g. of 2,6-dichloroisonicotinoyl chloride. The mixture is stirred 6 hours, cooled in an ice bath, acidified and worked up as in Example 1. Recrystallization from ethanol/water produces 12.5 g. of white, crystalline N-(2,6-dichloronicotinoyl)-l-aspargine; m.p. 187°–8° C.

(b) When 2,6-dibromoisonicotinoyl chloride is used in an equimolar amount to the above dichloro- derivative, N-(2,6-dibromoisonicotinoyl)-l-aspargine is obtained in a comparable yield.

EXAMPLE 4

To 60 ml. of an ice bath cooled aqueous solution containing 4.14 g. of glycine-N',N'-dimethylamide hydrochloride and 2.4 g. of NaOH is added 6.3 g. of 2,6-dichloroisonicotinoyl chloride. Proceeding in accordance with Example 3 produces 3.2 g. of pure N-(2,6-dichloroisonicotinoyl)-N',N'-dimethylglycinamide; m.p. 163°–4° C.

EXAMPLES 5–34

The following examples are made in accordance with the above detailed descriptions. The compounds made, their melting points (m.p.) in °C. and recrystallization solvents (X-solvent) are listed in Table I below. In all instances, the microanalyses confirmed the expected empirical formula. The compounds are identified in accordance with formula I. In some instances, the optical designation of the aminoacid is indicated in the customary fashion; in other instances, no optical isomers exist or the example refers to the d,l-mixture.

TABLE I

| Ex. # | Z | X | R | R' | | m.p. | X-solvent |
|---|---|---|---|---|---|---|---|
| 5 | Cl | $CH_2$ | $NH_2$ | H | | 219-20 | $EtOH/H_2O$ |
| 6 | Cl | $(CH_2)_2$ | OH | H | | 152-4 | $EtOH/H_2O$ |
| 7 | Cl | Y = alanine | | H | | 195-7 | $EtOH/H_2O$ |
| 8 | Cl | Y = glycine | | Me | | 196-8 | $EtOH/H_2O$ |
| 9 | Cl | Y = phenylalanine | | H | | 159-60 | $iPr/H_2O$ |
| 10 | Cl | Y = proline | | H | (1) | 154-5 | benzene |
| 11 | Cl | 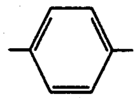 | OH | H | | 274-5 | $EtOH/H_2O$ |
| 12 | Cl | Y = aspartic acid | | | | glass | $H_2O$ |
| 13 | Cl | $C(Me)_2$ | OH | H | | 172-3 | $CHCl_3$ |
| 14 | Cl | Y = alanine | | H | (1) | 172-3 | $EtOH/H_2O$ |
| 15 | Cl | Y = valine | | H | | 167-8 | $CHCl_3$ |
| 16 | Cl | Y = methionine | | H | (1) | 111-2 | $CHCl_3$ |
| 17 | Cl | Y = glutamine | | H | (1) | 172-2 | $H_2O$ |
| 18 | Cl | Y = serine | | H | (1) | 176-7 | $EtOH/H_2O$ |
| 19 | Cl | $CH_2$ | NHiPr | H | | 176-8 | $EtOH/H_2O$ |
| 20 | Cl | $CH_2$ | $NHC_6H_5$ | H | | 227-8 | EtOH |
| 21 | Cl | Y = valine | | H | (1) | 85-7 | benzene |
| 22 | Cl | $CH_2$ | NHMe | H | | 175-6 | EtOH |
| 23 | Cl | $CH_2$ | NHEt | H | | 173-4 | EtOH |
| 24 | Cl | $CH_2$ | $NEt_2$ | H | | 132-3 | EtOH |
| 25 | Cl | $CH_2$ | NHBu | H | | 116-7 | EtOH |
| 26 | Cl | $(CH_2)_5$ | OH | H | | 118-20 | EtOH |
| 27 | Cl | 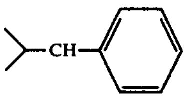 | OH | H | | 187-8 | EtOH |
| 28 | Cl | 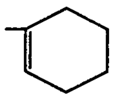 | OH | H | | 258-60 | EtOH |
| 29 | Cl | Y = tryptophan | | H | (1) | 254-5 | EtOH |
| 30 | Cl | Y = phenylalanine | | H | (1) | 185-7 | EtOH |
| 31 | Cl | Y = methionine | | H | | 155-6 | EtOH |
| 32 | Br | Y = alanine | | H | (1) | 183-4 | $EtOH/H_2O$ |
| 33 | Br | Y = methionine | | H | (1) | 139-40 | $EtOH/H_2O$ |
| 34 | Br | Y = phenylalanine | | H | (1) | 166-7 | $EtOH/H_2O$ |

EXAMPLE 35

In a pre-emergence herbicidal test on common weeds and crops, a spray-formulation was made up by first preparing a 50,000 ppm stock suspension in proportions of 200 mg. of I, 1 ml. of DMF and 3 ml. of isopropanol containing 4% polyethylene sorbitan mono-oleate. Before use, this suspension was diluted with 50% $H^2O$-/acetone (by volume) to give a solution or sprayable dispersion containing 10 mg. I/ml. This composition was sprayed through a fan-nozzle sprayer calibrated to deliver 10 lbs./acre. The flats are planted with the test seeds shortly before administration of I in pasteurized soil treated with a fungicide. The flats were then watered lightly for 24 hours while stored in a greenhouse. The results are shown in Table II, using the following codes:

A. Growth accelleration
B. Burn or contact injury
C. Chlorosis (1-3) to necrosis (4-8) to death (9-10)
D. Defoliation
E. Emergence inhibited
F. Earlier flowering
G. Growth retarded
H. Hormone effect
K. Axillary stimulation L. Leaf malformation
T. Selective burning of growing tissue The degree of response is indicated by 0 for no response, 10 for maximum and various degrees between shown by 1-9. NT stands for not tested.

The plants are identified as follows:
I Velvet leaf
II Johnson grass
III Giant foxtail
IV Quackgrass
V Pigweed
VI Yellow nut grass
VII Corn
VIII Curly dock
IX Cheat grass
X Soybean

TABLE II

| Compd. of Ex. # | I | II | III | IV | V | VI | VII | VIII | IX | X |
|---|---|---|---|---|---|---|---|---|---|---|
| 1 (a) | 0 | 0 | 4G | 0 | 0 | 3G | 0 | 0 | 4G | 3H4G |
| 1 (b) | 0 | 0 | 0 | 0 | 5G | 0 | 0 | 4G | 0 | 0 |
| 2 | 0 | 0 | 0 | 0 | 10E | 0 | 5E | 6G | 0 | |
| 3 (a) | 0 | 10E | 5G | 10E | 10E | 10E | 0 | 10E | 10E | 10E |
| 4 | 0 | 5E | 0 | 0 | 0 | 3G | 0 | 0 | 0 | 10E |
| 5 | 0 | 5G | 0 | 5E5G | 3C5G | 5G | 4G | 10C | 5G | 3L5G |

TABLE II-continued

| Compd. of Ex. # | I | II | III | IV | V | VI | VII | VIII | IX | X |
|---|---|---|---|---|---|---|---|---|---|---|
| 6 | 0 | 5G | 3G | 0 | 3G | 5G | 4G | 5G | 3G | 6G |
| 7 | 0 | 0 | 0 | 10E | 9C | 10E | 4G | 0 | 0 | 4G |
| 8 | 0 | 0 | 5G | 10E | 10E | 10E | 0 | 5E5G | 0 | 0 |
| 9 | 0 | 0 | 0 | 7E | 0 | 0 | 0 | 5G | 0 | 0 |
| 10 | 0 | 0 | 0 | 0 | 4G | 0 | 4G | 0 | 0 | 10E |
| 11 | 0 | 0 | 0 | 8E5G | 0 | 3G | 0 | 0 | 0 | 4G |
| 12 | 0 | 0 | 4G | 8E | 3H | 0 | 3H4G | 5G | 0 | 3C5G |
| 13 | 0 | 0 | 4G | 5E | 10E | 0 | 0 | 0 | 0 | 3H |
| 14 | 0 | 0 | 4G | 8E | 0 | 0 | 0 | 0 | 0 | 3C |
| 15 | 0 | 0 | 8E | 10E | 10E | 0 | 0 | 0 | 0 | 0 |
| 16 | 0 | 0 | 0 | 0 | 0 | 4G | 4G | 0 | 0 | 3L3G |
| 17 | 5E | 0 | 0 | 5E | 0 | 6G | 0 | 5G | 0 | 4G |
| 18 | 0 | 4G | 0 | 8E5G | 0 | 5G | 0 | 4G | 0 | 10E |
| 19 | 5E | 0 | 0 | 0 | 0 | 10E | 0 | 0 | 0 | 5G |
| 20 | NT | NT | NT | NT | NT | NT | NT | NT | NT | NT |
| 21 | 0 | 0 | 0 | 0 | 7C | 0 | 0 | 5E | 0 | 0 |
| 22 | 5E | 0 | 0 | 0 | 0 | 10E | 0 | 0 | 0 | 0 |
| 23 | 0 | 0 | 0 | 0 | 0 | 0 | 0 | 0 | 0 | 10E |
| 24 | 0 | 0 | 0 | 0 | 0 | 10E | 0 | 0 | 0 | 7E |
| 25 | 0 | 0 | 0 | 0 | 0 | 5G | 0 | 0 | 0 | 10E |
| 26 | 0 | 0 | 4G | 0 | 0 | 0 | 3G | 0 | 0 | NT |
| 27 | 0 | 0 | 0 | 0 | 10E | 0 | 0 | 0 | 0 | NT |
| 28 | 0 | 0 | 0 | 0 | 0 | 0 | 3A | 5G | 0 | 3G |
| 29 | 0 | 5E | 7E5G | 0 | 0 | 4G | 0 | 0 | 0 | NT |
| 30 | 0 | 0 | 0 | 4G | 0 | 0 | 0 | 10E | 0 | 0 |
| 31 | 0 | 0 | 0 | 5E | 0 | NT | 0 | 0 | 0 | 0 |
| 32 | 0 | 0 | 0 | 0 | 0 | 0 | 0 | 0 | 5E | 7E |
| 33 | 0 | 0 | 0 | 0 | 0 | NT | 0 | 0 | 0 | 10E |
| 34 | 0 | 0 | 0 | 0 | 0 | NT | 0 | 0 | 0 | 3L |

EXAMPLE 36

Stock solutions described in Example 35 are prepared and diluted in the same fashion. The final compositions are topically applied as dilute aqueous suspension at the rate of 10 lbs. of I/acre of soil for post-emergence herbicidal activity. The plants are placed in a greenhouse but without overhead irrigation for the first 24 hours.

The results are shown in Table III, using the codes described above. The plants used in this test are XI Tomato
XII Nutgrass
XIII Snapbean
XIV Bindweed
XV Wheat
XVI Johnson grass

TABLE III

| Compd. of Ex. # | XI | XII | XIII | XIV | XV | XVI |
|---|---|---|---|---|---|---|
| 1a | 3H4G | 4G | 3H5G | TN | 0 | 0 |
| 1b | 10B | 0 | 8B | 2B | 3C | 0 |
| 2 | 0 | 0 | 0 | 0 | 0 | 0 |
| 3 (a) | 2L | 0 | 3L | 5B | 0 | 0 |
| 4 | 3B5G | 0 | 0 | 3C | 0 | 0 |
| 5 | 5G | 0 | 4G | 0 | 0 | 0 |
| 6 | 9B | 3C | 9B | 4B | 4C | 0 |
| 7 | 5H4G | 0 | 4H5G | NT | 0 | 0 |
| 8 | 3B4G | 0 | 3B4G | NT | 0 | 0 |
| 9 | 4G | 0 | 0 | NT | 0 | 0 |
| 10 | 3H5G | 0 | 7D | NT | 4G | 0 |
| 11 | 3H5G | 0 | 3H3G | NT | 0 | 0 |
| 12 | 0 | 0 | 10E | NT | 0 | 3C |
| 13 | 3H | 0 | 3H4G | NT | 0 | 0 |
| 14 | 9C | 0 | 4G | NT | 0 | 0 |
| 15 | 4B | 0 | 3B | NT | 3B | 0 |
| 16 | 4B | 0 | 3B/F | 4B | 2B | 0 |
| 17 | 4H3G | 2B | 2B/F | 3B | 0 | 0 |
| 18 | 4B5G | 0 | 2B/F | 2B | 0 | 0 |
| 19 | 8B | 0 | 3L/F | 2B | 0 | 0 |
| 20 | NT | NT | NT | NT | NT | NT |
| 21 | 2B4H | 0 | 4D | 3B | 0 | 0 |
| 22 | 2T | 0 | 3B3G | 5B | 0 | 0 |
| 23 | 3B5G | 0 | 3H | 2B | 0 | 0 |

TABLE III-continued

| Compd. of Ex. # | XI | XII | XIII | XIV | XV | XVI |
|---|---|---|---|---|---|---|
| 24 | 2B3H | 0 | 0 | 0 | 0 | 0 |
| 25 | 10B | 2B | 3B/F | 3B | 0 | 2B |
| 26 | 0 | 0 | 4H | 0 | 0 | 0 |
| 27 | 3H | 0 | 5T4G | 3B | 0 | 0 |
| 28 | 3H | 0 | 3B3H | 4C | 0 | 0 |
| 29 | 0 | 0 | 3H | 0 | 0 | 0 |
| 30 | 10B | 0 | 8B | 2B | 0 | 0 |
| 31 | 2B5G | 2B | 2B3H | NT | 2B | 2B |
| 32 | 0 | 0 | 5T | 0 | 0 | 0 |
| 33 | 0 | NT | 3K | 0 | 0 | 0 |
| 34 | 3A | NT | 3T3L | 0 | 3C | 0 |

In addition to the above activities, all the compounds also show activity as plant growth regulators and many are useful as abscission compounds as demonstrated by the test described in U.S. Pat. No. 3,932,453. In this test, compounds of Examples 5, 10, 12, 13 and 21 are outstanding at 250 ppm; A 50% or greater reduction in pull-force is required for the compounds of Examples 1(b), 7, 14, 17, 18 and 20.

Also, many of the above compounds were tested in accordance with the test described in U.S. Pat. No. 3,487,961 for carbohydrate enhancement. Thus, compounds 1(a), 6, 9 and 12 show pole percent cane values of 8.16, 8.26, 7.01 and 7.02 in the fourth week with juice purity values of 71.16, 72.26, 63.77 and 68.01 respectively; the purity of the control is 64.18 with a pole percent cane of 6.81.

The above shown method of preparing an agricultural stock solution or concentrate is, of course, only one of many ways to prepare such a product. Those skilled in the art will be cognizant of many other ways to prepare a liquid or solid concentrate containing between 10,000 and 100,000 ppm of I. Solid supports for I can be selected from finely divided bentonite, kieselguhr, fuller's earth, silica, etc. Homogeneous mixtures of I and a solid support or solutions or dispersions of I can then be diluted at the site of the user for administration as a spray dust or a liquid spray at a concentration suitable for the method of administration to insure the desired 5-20 lbs./acre delivery to the crop. In both, the liquid and the dust spray, customarily used additives for such materials are found to be well compatible with I, e.g., suspending agents, wetting agents, stabilizers, buffers or the like. In many instances, it may be advantageous to use I in the form of an acid addition salt. Particularly suitable salts are the hydrochlorides, hydrobromides, phosphates, sulfates and/or nitrates. Organic salts can also be used, but most of the organic acids are less advantageous because of higher cost and possible lower stability than mineral acid salts. These salts impart higher water solubility which makes the preparation of liquid concentrates of I particularly simple; e.g., solutions containing the usual additives can be used as concentrates with 10,000-100,000 ppm of I (1-10% weight/volume) and, of course, are easily diluted to the desired spray concentration at the administration site.

We claim:

1. A compound of the formula

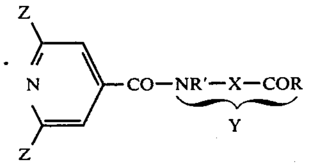

wherein Z is Br or Cl, R is OH, $NH_2$, NH-loweralkyl, NH-phenyl or N-diloweralkyl, R is H or $CH_3$, X is phenylene, >$C(CH_3)_2$, >$CHCH_2CONH_2$, $-(CH_2)_n$,

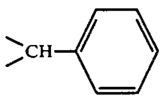 or 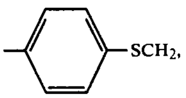

with n being an integer from 2-5, or wherein the moiety embraced as Y represents the acyl portion of a naturally occuring amino acid, and agriculturally acceptable acid addition salts thereof.

2. A compound of claim 1 wherein Z is chlorine.

3. The compound of claim 2 wherein Y represents a natural aminoacid.

4. The compound of claim 2 wherein X is $CH_2$, R' is H and R is NHMe.

5. The compound of claim 2 wherein X is $CH_2$, R' is H and R is OH.

6. The compound of claim 2 wherein X is $CH_2$, R' is $CH_3$ and R is OH.

7. The compound of claim 2 wherein X is $CH_2COOH$, R' is H and R is OH.

8. The compound of claim 2 wherein X is $CH_2$, R' is H and R is $NH_2$.

9. The compound of claim 2 wherein X is $—CH_2CH_2—$, R' is H and R is OH.

10. A herbicidal composition containing as an active ingredient, a compound of the formula

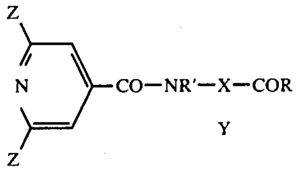

wherein Z is Br or Cl, R is OH, $NH_2$, NH-loweralkyl, NH-phenyl or N-diloweralkyl, R is H or $CH_3$, X is phenylene, >$C(CH_3)_2$, >$CHCH_2CONH_2$, $-(CH_2)_n$,

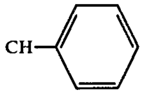 or 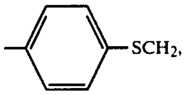

with n being an integer from 2-5, or wherein the moiety embraced as Y represents the acyl portion of a naturally occuring amino acid, and agriculturally acceptable acid addition salts thereof, together with an agriculturally acceptable diluent.

11. The composition of claim 10 wherein said diluent is water.

12. The composition of claim 11 wherein Z is chlorine.

13. The composition of claim 12 wherein Y represents a natural aminoacid.

14. The composition of claim 12 wherein X is $CH_2$, R' is H and R is NHMe.

15. The composition of claim 12 wherein X is $CH_2$, R' is H and R is OH.

16. The composition of claim 12 wherein X is $CH_2$, R' is Me and R is OH.

17. The composition of claim 12 wherein X is $CH_2COOH$, R' is H and R is OH.

18. The composition of claim 12 wherein X is $CH_2$, R' is H and R is $NH_2$.

* * * * *